US012806600B2

(12) United States Patent
Reyhanitash et al.

(10) Patent No.: US 12,806,600 B2
(45) Date of Patent: Nov. 24, 2026

(54) PROCESS FOR THE ISOLATION OF AMINES

(71) Applicant: Givaudan SA, Vernier (CH)

(72) Inventors: Ehsan Reyhanitash, Hilversum (NL); Stephan Haiber, Almere (NL)

(73) Assignee: GIVAUDAN SA, Vernier (CH)

( * ) Notice: Subject to any disclaimer, the term of this patent is extended or adjusted under 35 U.S.C. 154(b) by 250 days.

(21) Appl. No.: 18/284,973

(22) PCT Filed: Apr. 21, 2022

(86) PCT No.: PCT/EP2022/060483

§ 371 (c)(1),
(2) Date: Sep. 29, 2023

(87) PCT Pub. No.: WO2022/223659

PCT Pub. Date: Oct. 27, 2022

(65) Prior Publication Data

US 2024/0189795 A1 Jun. 13, 2024

(30) Foreign Application Priority Data

Apr. 21, 2021 (EP) .................................... 21169717

(51) Int. Cl.
*B01J 20/26* (2006.01)
*B01J 20/28* (2006.01)
(Continued)

(52) U.S. Cl.
CPC ....... *B01J 20/261* (2013.01); *B01J 20/28026* (2013.01); *B01J 20/3071* (2013.01);
(Continued)

(58) Field of Classification Search
None
See application file for complete search history.

(56) References Cited

U.S. PATENT DOCUMENTS

2005/0184062 A1* 8/2005 Kobayashi ......... B01J 20/28009 219/680
2014/0024127 A1* 1/2014 Watando .................. B01J 49/06 436/98
(Continued)

FOREIGN PATENT DOCUMENTS

DE 202007008841 U1 * 6/2008 .......... B01J 20/3204
JP 2000140654 A 5/2000
(Continued)

OTHER PUBLICATIONS

Sobiech et al. (Materials Today Communications, 2020, 22, 100739). (Year: 2020).*
(Continued)

*Primary Examiner* — Clare M Perrin
(74) *Attorney, Agent, or Firm* — Curatolo Sidoti & Trillis Co., LPA; Floyd Trillis, III; Salvatore A. Sidoti

(57) ABSTRACT

There is provided a method for the isolation of an amine from an aqueous solution thereof, comprising the steps of:

Figure 1A:
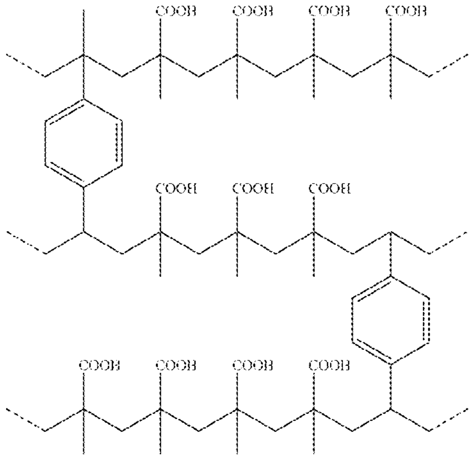

a) contacting the aqueous solution of the amine with an adsorbent functionalized with carboxyl groups;
b) removing water from the adsorbent; and
c) thermaly desorbing the amine.

The method is particularly suitable for the isolation of ethanolamine.

20 Claims, 2 Drawing Sheets

(51) Int. Cl.

| | |
|---|---|
| ***B01J 20/30*** | (2006.01) |
| ***B01J 20/34*** | (2006.01) |
| ***C02F 1/28*** | (2023.01) |
| ***C07C 213/10*** | (2006.01) |
| ***C12P 13/00*** | (2006.01) |
| *C07C 209/10* | (2006.01) |
| *C07C 227/38* | (2006.01) |

(52) U.S. Cl.
CPC ........... *B01J 20/3483* (2013.01); *C02F 1/285* (2013.01); *C07C 213/10* (2013.01); *C12P 13/001* (2013.01); *C07C 209/10* (2013.01); *C07C 227/38* (2013.01)

(56) References Cited

U.S. PATENT DOCUMENTS

| | | | | |
|---|---|---|---|---|
| 2018/0272267 | A1* | 9/2018 | Kondo | C08F 214/06 |
| 2019/0160423 | A1* | 5/2019 | Yoon | B01D 53/0423 |
| 2021/0252421 | A1* | 8/2021 | Cannell | B01D 3/001 |

FOREIGN PATENT DOCUMENTS

| | | | | |
|---|---|---|---|---|
| KR | 101766861 | B1 | 8/2017 | |
| WO | 2007144346 | A1 | 12/2007 | |
| WO | WO-2008013370 | A1 * | 1/2008 | C02F 1/048 |
| WO | 2020011725 | A1 | 1/2020 | |

OTHER PUBLICATIONS

Bashtani et al. (Microchimica Acta, 2018, 185, 14). (Year: 2018).*
Machine translation of DE-202007008841-U1, pp. 1-14. (Year: 2008).*
Wang et al. (Desalination and Water Treatment, 2020, 182, 320-331). (Year: 2020).*
Suresh et al. (Chemical Industry & Chemical Engineering Quarterly, 2013, 19(2), 195-212). (Year: 2013).*
Bandosz et al. (Analytical Chemistry, 1992, 64, 891-895). (Year: 1992).*
Dow, "Ethanolamines", 2003, pp. 1-18). (Year: 2003).*
International Search Report for Application No. PCT/EP2022/060483, dated Aug. 30, 2022.
International Written Opinion for Application No. PCT/EP2022/060483, dated Aug. 30, 2022.
European Patent Office Search Report for application No. 21169717.2, dated Oct. 4, 2021.
Xiaomei Wang et al., "Carboxyl functionalized hyper-cross-linked dendrimers and their adsorption of aniline from aqueous solution", Desalination and Water Treatment, vol. 182, pp. 320-331, Apr. 2020.

* cited by examiner

PROCESS FOR THE ISOLATION OF AMINES

CROSS REFERENCE TO RELATED APPLICATIONS

This application is a national stage application of International Application No. PCT/EP2022/060483, filed 21 Apr. 2022, which claims priority from European Application No. 21169717.2, filed 21 Apr. 2021, both of which applications are incorporated herein by reference.

TECHNICAL FIELD

The present invention relates generally to a method to purify amines from aqueous solutions, in particular from diluted aqueous solutions thereof. The present invention also relates to the products of said purification method and the various uses of these products.

BACKGROUND

Amines are compounds formally derived from ammonia, wherein one, two or three hydrogen atoms have been replaced by a substituent, leading to primary, secondary or tertiary amines.

Typically, the substituent is an alkyl or aryl group, which can optionally bear a further functional group, for example a hydroxyl group, a halogen atom, or others. Amines are widely used in different fields.

Hydroxylamines, also called aminoalcohols, contain a hydroxyl group in addition to the amino group. They are widely used in industrial applications, for example as solvents, synthetic intermediates, and high-boiling bases.

A particular hydroxylamine is ethanolamine ($HO—CH_2—CH_2—NH_2$) which is used for a wide variety of applications, including as a raw material precursor for flavour products. Ethanolamine can also be used for the recovery and removal of acidic gases from natural, fuel and process gas, for the production of monoalkanolamides for non-ionic detergents, emulsifiers and soaps, and for the synthesis of acylethanolamine, phenylethanolamine and 2-mercaptothiazole in the manufacture of various products.

Ethanolamine is currently produced on an industrial scale by reacting ethylene oxide with an excess of ammonia. However, this is not a natural process and therefore cannot be used to produce natural flavour components. WO 2007/144346, the contents of which are incorporated herein by reference, discloses a natural process for making ethanolamine involving fermentation of an ethanolamine-producing bacterium. WO 2020/011725 refers to isolation of ethanolamine from fermented composition by distillation methods in order to obtain naturally produced ethanolamine in food grade.

It is therefore desirable to provide new and/or improved methods for purifying amines, in particular hydroxylamines from aqueous compositions, for example from waste water or from fermentation compositions.

SUMMARY

In accordance with a first aspect of the present invention there is provided a method for the isolation of an amine from an aqueous solution thereof, comprising the steps of:

a) contacting the aqueous solution of the amine with an adsorbent functionalized with carboxyl groups;
b) removing water from the adsorbent; and
c) thermally desorbing the amine.

In accordance with a second aspect of the present invention there is provided in particular a method for the isolation of ethanolamine from an aqueous solution thereof.

Certain embodiments of any aspect of the present invention may provide one or more of the following advantages:

economical access to amines provided in diluted solutions; in particular
lower energy demand of the separation process;
reduction of needed solvents;
high purity of the desired amine;
higher yield of the desired amine; and
straightforward scale-up to increase throughput.

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

DETAILED DESCRIPTION

The present invention is based on the surprising finding that amines can be efficiently isolated from aqueous solutions by an adsorption/desorption sequence using a functionalized adsorbent.

There is therefore provided herein a method for the isolation of an amine from an aqueous solution thereof, comprising the steps of:

a) contacting the aqueous solution of the amine with an adsorbent functionalized with carboxyl groups;
b) removing water from the adsorbent; and
c) thermally desorbing the amine.

By this method, the amine can be obtained in pure form, and no further step of solvent separation or elimination is required.

Adsorption is an affinity separation method suitable for separation of substances from diluted solutions. After adsorption, the adsorbate has to be desorbed from the adsorbent to complete the isolation process and to regenerate the adsorbent.

As used herein, the term "aqueous solution" refers to an aqueous solution comprising one or more amines in any possible amount or concentration. The possible concentration is determined by the solubility of a particular amine in water.

The term "dilute aqueous solution" refers to an aqueous solution comprising the amine in a concentration range up to 5% by weight or lower, for example up to 4% by weight, or up to 3% by weight. For example, the concentration of the amine can be as high as possible, but limited by the solubility of the amine. Another upper limit can be the concentration of the amine where it becomes harmful to the microorganisms responsible for the formation process.

As used herein, the term "adsorption" refers to the process of adhesion of amines to the adsorbent by formation of a complex between the amine and the carboxyl group of the adsorbent. By said complex formation, the amine is retained at the adsorbent.

As used herein, the term "adsorbent" refers to a suitable medium able to adsorb a particular substance that was brought in contact with. In other words, it is able to retain or to accumulate the adsorbate on its surface. In the present invention, the adsorbent is a matrix or a carrier functionalized with carboxyl groups which can form a complex with the amine groups of the adsorbate. The matrix or the carrier of the adsorbent can be a porous material like silica gel, zeolithes, or a polymeric adsorbent, for example based on poly(meth)acrylate or polystyrene.

As used herein, the term "adsorbate" refers to the substance that is adsorbed, that is the amine.

As used herein, the term "desorption" refers to the reverse of adsorption, which means that the adsorbate is released from the adsorbent.

In step a) of the method of the present invention, the aqueous solution of the amine is contacted with an adsorbent functionalized with carboxyl groups. By this contacting the formation of a complex between the amine and the carboxyl groups of the adsorbent is enabled. The major part of the aqueous solution is water, which does not interact further with the adsorbent and can be removed. As used herein, the term "contacting" means every possible technique to bring the aqueous solution together with the adsorbent, for example admixing, pumping, loading etc.

When the aqueous solution comprises further chemical compounds, a selectivity of the adsorbent for the main compound of interest but not for the further chemical compounds is required. However, if such selectivity is not given, further separation or purification steps might be applied after isolation of the main compound in mixture with one or more further chemical compounds from aqueous solution. For example, if the aqueous solution comprises different amines, the present method will allow for the isolation of the mixture of amines, but not necessarily the individual amines. Their separation can be achieved subsequently by other techniques.

The pH of the aqueous solution needs to be controlled, as the amine functionalities should not be protonated to allow for complex formation with the carboxylic groups of the adsorbent. The amine containing aqueous solution should have a pH of above the $pK_a$ of the amine to ensure that at least 50% of the amine is available for adsorption.

The amount of amines that can be removed from an aqueous solution depends on the capacity of the adsorbent. As used herein, the term "capacity", describes the effectiveness of adsorption. It is often defined as the mass of adsorbate per kilogram of adsorbent. When the capacity limit of the adsorbent is reached, in other words, when all carboxyl groups are occupied, the adsorbent cannot uptake further adsorbate. This full load can be monitored, for example continuously by conductivity measurement at the outlet of the column, or by gas chromatography of individual samples of the eluent. At the full load point, also called the breakthrough point, the amine concentration at the outlet quickly increases to the inlet amine concentration.

Optionally, after contacting the aqueous solution of the amine with an adsorbent functionalized with carboxyl groups, a washing step is added. For example, the loaded adsorbent is washed with water to remove residues, for example salts present in the aqueous solution. With this optional step, the salts are removed and are not present in the final product obtained after completion of the presented method.

In step b) of the method of the present invention, water is removed from the adsorbent. In a first step it can be removed by draining, decanting, by flushing with air or nitrogen, preferably with compressed air or nitrogen. In a further step, remaining water is removed by flushing with compressed preheated nitrogen. Water removal is completed, once the nitrogen stream which is flowing through a cooled and efficient condenser, does not carry water anymore, so no condensation takes place anymore.

In step c) of the method of the present invention, the adsorbed amine is thermally desorbed from the adsorbent. So once the water is removed, the temperature of the system is elevated to reverse the amine-carboxyl complex. The amine is deliberated and can be collected, for example by condensation in pure form.

It is an advantage of the present method that the amine can be obtained in pure form by thermal desorption. No further step of solvent separation or elimination is required. An alternative method to the direct desorption of the amine is to wash it out using a suitable solvent. However, the amine would be provided in solution, and an additional separation step would become necessary.

In one specific embodiment the amine is an alkanol amine, also called aminoalcohol. Alkanol amines contain hydroxyl and amino functional groups, and are useful for many industrial applications, in particular the 2-aminoalcohols.

In one specific embodiment the alkanol amine is ethanolamine.

In a further embodiment the adsorbent is thermally stable up to at least 150 °C, preferably stable up to at least 160 °C, or even stable up to at least 170 °C. This allows for handling of the adsorbent at elevated temperatures, in particular during the removal of water (step b) and the desorbing of the amine (step c).

In a further embodiment the step b), the step of removing water, comprises flushing out of the container comprising the adsorbent with a compressed nitrogen stream, while the nitrogen stream or the container comprising the adsorbent are heated up to an elevated temperature.

For example, the nitrogen stream for removing water is heated up to at least 70 °C, or up to 80 °C, or up to 90 °C, or up to 100 °C.

For example, for removing water the container comprising the adsorbent is heated up to at least 80 °C, preferably up to 90 °C, or up to 100 °C, or up to 110 °C.

In a further embodiment the step b), the step of removing water, comprises flushing out of the container comprising the adsorbent with a compressed nitrogen stream, while the nitrogen stream and the container comprising the adsorbent are independently heated up to an elevated temperature, the nitrogen stream for example up to at least 70 °C, or up to 80 °C, or up to 90 °C, or up to 100 °C, and the container comprising the adsorbent for example up to at least 80 °C, preferably up to 90 °C, or up to 100 °C, or up to 110 °C.

In a further embodiment the step b) comprises flushing out of the container comprising the adsorbent with a compressed nitrogen stream, while the nitrogen stream is heated up to about 70 °C and the container comprising the adsorbent is heated up to about 110 °C.

Water removal is completed, once the nitrogen stream which is flowing through a cooled and efficient condenser, does not carry water anymore, so no condensation takes place anymore.

In a further embodiment of the present invention, thermal desorption of the amine in step c) takes place at elevated temperature. This temperature should be above the boiling point of water and sufficient to provide the activation energy/binding energy of the amine-carboxyl complex. On the other hand, its upper limit should be below the temperature required for the formation of a covalent amide bond. Said amide bond is not reversible, and is therefore deactivating the carboxyl functionalities of the adsorbent. Formation of amides has to be minimized in order to reuse the adsorbent in multiple adsorption-desorption cycles. The optimal temperatures might vary slightly for the given amines and alkanolamines, but are all in a similar range.

Finally, any operation should be carried out below the maximum operating temperature of the adsorbent.

For example, the desorption step c) should be carried out at a temperature in a range between 100 °C and 150 °C, preferably between 105 °C and 145 °C, more preferably between 110 °C and 140 °C.

To ensure the temperature during the thermal desorption step c), the nitrogen stream or the container comprising the adsorbent are heated up to an elevated temperature.

For example, the nitrogen stream for desorption of the amine is heated up to at least 100 °C, or up to 110 °C, or up to 120 °C, or up to 130 °C, or up to 140 °C, or up to 150 °C.

For example, for desorption of the amine the container comprising the adsorbent is heated up to at least 120 °C, or up to 130 °C, or up to 140 °C, or up to 150 °C, or up to 160 °C, or up to 170 °C.

In a further embodiment the step c) is carried out while the nitrogen stream and the container comprising the adsorbent are independently heated up to an elevated temperature, the nitrogen stream for example up to at least 100 °C, or up to 110 °C, or up to 120 °C, or up to 130 °C, or up to 140 °C, or up to 150 °C, and the container comprising the adsorbent for example up to at least 120 °C, or up to 130 °C, or up to 140 °C, or up to 150 °C, or up to 160 °C, or up to 170 °C.

In a further embodiment the step c) is carried out while the nitrogen stream is heated up to about 110 °C and the container comprising the adsorbent is heated up to about 170 °C For example, the desorbed amine is collected in a cooled condenser. The temperature of the condenser can be adjusted to the amine to be isolated, for example to temperatures below 10 °C, preferably below 5 °C or lower.

In a further embodiment the adsorbent has a porous polymethacrylate matrix. Said matrix is robust, it tolerates handling at higher temperatures, under pressure, at different pH conditions. Alternatively, the matrix of the adsorbent can be chosen from the group consisting of silica gel, zeolites, or a polymeric adsorbent, like polyacrylate or polystyrene.

In a further embodiment of the present invention, the adsorbent is provided in a container which is selected according to the mode of the method. For example, the container can be a column, a vessel, a beaker etc.

For example, if the container is a column, the method can be carried out by pumping the aqueous solution through the column while in steps b) and c) a nitrogen stream, for example a compressed nitrogen stream can be applied. Alternatively, the method can be carried out with the adsorbent provided in a beaker. The aqueous solution can be simply admixed first, and drained in step b, followed by simple heating in step c). The choice of the container and the operation mode will contribute to the efficiency of the method.

Adsorbents can show a significant volume expansion when adsorbing amines. The potential volume expansion can be determined beforehand using the adsorbent in a container with sufficient free volume above the adsorbent bed. For example, the volume expansion can be measured as increase of height of the adsorbent bed, when fully saturated with the amine. For example, Diaion™ WK11 adsorbent expands by ~60% of its initial height when adsorbing ethanolamine. From this measurement, the relative volume expansion can be calculated for any volume to be used, and so the appropriate amount of adsorbent can be calculated. By taking the volume expansion of the adsorbent into account, the experimental setup can be optimized, for example by an optimized loading of a column with the adsorbent. This is of particular importance if the method is used on industrial scale.

In a further embodiment of the present invention, the adsorbent can be used in multiple adsorption-desorption sequences, thereby further enhancing the economic advantages of the method.

In a further embodiment the aqueous solution is a fermentation composition. Alternatively, the aqueous solution is wastewater from any industrial process. It might be of interest to obtain purified amines, to provide purified water, or both.

In a further embodiment, the provided method results in the amine having a purity equal to or greater than about 60%, or greater than about 70%, preferably greater than about 80%, even more preferably greater than about 90%, or even more preferably greater than about 95%. For example, the amine contains water only, in particular if an optional washing step was carried out after completion of step a) of the method.

In a further embodiment, the provided method offers access to a purified amine in a yield of equal to or greater than about 80% or more, for example equal to or greater than about 85% or even 90%.

The purity of the amine and its yield are highly dependent on the efficiency of the method and can be influenced by process parameters. For example, if the method is carried out in a column, the column design plays an important role. As the adsorption step (a) is highly efficient and much less sensitive than the desorption step (c), the column design parameters will be mostly defined by and optimized for the desorption step. The three major design parameters are i) the column diameter to maximize the heat transfer from the jacket and the nitrogen stream, ii) the jacket temperature and iii) the nitrogen stream temperature to optimize the heat transfer. The cumulative effect of optimizing these three design parameters will be a maximized amine desorption and a minimized amide formation. Example 3 introduces a technique to measure the influence of any adjustment to these three design parameters, as demonstrated for ethanolamine.

A process comprising the described method can be easily scaled up from a pilot scale to a commercial scale, for example by adding several identical columns in parallel to form a bundle of identical columns, all of which contain a suitable adsorbent. Such a bundle can be encased in a structure serving as the heating jacket for the entire bundle. The heating medium required during the steps (b) and (c) is then circulated through this encasing structure. A similar design is available for heat exchangers and is referred to as a shell and tube heat exchanger. As an analogy, the adsorbent-containing columns can be compared with the tubes of a shell and tube heat exchanger and the encasing structure can be compared with the shell of a shell and tube heat exchanger. The amine-containing solution can be distributed among the bundle of adsorbent-containing columns using a fluid distributer, the design of which is also familiar for the manufactures of shell and tube heat exchangers.

In a further embodiment, the method for the isolation of ethanolamine further comprises the synthesis of ethanolamine by fermenting a carbon source in the presence of an ethanolamine-producing microorganism in order to provide a fermentation composition comprising ethanolamine. The described method gives a fully natural process to provide ethanolamine, when beginning from natural materials coming from natural sources.

EXAMPLES

General

Ethanolamine (≥99%) and HCl (1 M) were supplied by Merck KGaA. Demineralized water was produced by a Milli-Q® laboratory water purification system with a resistivity of 18.2 MΩ.cm. The adsorbents, Diaion™ WK11 and Diaion™ HP2MGL, were purchased from Alfa Aesar. An aqueous solution of ethanolamine at a concentration of 5 wt % was prepared for these experiments.

Example 1: Isolation of Ethanolamine Using a Functionalized Adsorbent Diaion™ WK11

Diaion™ WK11 (WK11) is a porous methacrylate-based adsorbent functionalized with carboxyl groups. Its chemical structure is shown in FIG. 1*a*. It is thermally stable up to 150 °C. When fully saturated with ethanolamine, theoretically, WK11 will demonstrate an adsorption capacity of ~550 g ethanolamine per 1 kg adsorbent.

The theoretical adsorption capacity QT($Q_{Theoretical}$) can be calculated as follows:

$$Q_{Theretical} = 2.9\frac{\text{meq}_{Adsorbate}}{\text{ml}_{Resin\ as\ shipped}} = 2.9\frac{\text{mol}_{Ethanolamine}}{\text{l}_{Resin\ as\ shipped}} \times 61.1\frac{\text{g}_{Ethanolamine}}{\text{mol}_{Ethanolamine}} \times \frac{1000}{0.66}\frac{\text{ml}_{Resin\ as\ shipped}}{\text{kg}_{Resin\ as\ shipped}} \times \frac{1}{0.5}\frac{\text{kg}_{Resin\ as\ shipped}}{\text{kg}_{Resin\ dry}} = 543\frac{\text{g}_{Ethanolamine}}{\text{kg}_{Resin\ dry}}$$

An aqueous solution of ethanolamine (5 wt %) was pumped through the column containing 20 g Diaion™ WK11 (used as received) at a flow rate of 2.5 mL/min, and samples were taken from the eluent over time to identify the breakthrough point. The liquid that remained in the column after pumping had stopped was flushed out of the column with a compressed nitrogen stream. A heating bath, using a silicon-based oil to preheat the compressed nitrogen stream to ~70 °C and heat the jacket to ~110 °C, was then used to remove the residual water from the column. The nitrogen stream, now carrying water vapor and minor amounts of ethanolamine vapor, was directed to a cooled condenser to 2 °C to condense the vapors and determine their ethanolamine content. The residual water was removed from the column in ~90 min. Thereafter, the heating bath was preheating the compressed nitrogen stream to ~110 °C and heating the jacket of the column to ~170 °C for the desorption stage to reverse carboxyl ethanolamine complexes and desorb molecular ethanolamine. The molecular ethanolamine was collected by directing the nitrogen stream, now carrying ethanolamine vapor, to the cooled condenser to 2 °C. The desorption stage lasted ~90 min.

The sequence of adsorption/water removal/desorption following the procedure described above was performed in multiple cycles. The observed ethanolamine capacities (in $g_{ethanolamine}/kg_{WK11}$), purities (in wt %) and desorption yields (in wt %) are shown in Table 1:

TABLE 1

| Cycle | Ethanolamine capacity [$g_{Ethanolamine}/kg_{Dry\ WK11}$] | Ethanolamine purity [wt %] | Desorption yield [wt %] |
|---|---|---|---|
| 1 | 458 | 95.4 | n.d.* |
| 2 | 149 | 96.1 | 89 |
| 3 | 167 | 96.3 | 91 |
| 4 | 179 | 97.2 | 94 |
| 5 | 145 | 95.6 | n.d.* |
| 6 | 188 | 98.6 | n.d.* |

n.d.*: not determined

As can be seen in Table 1, an adsorption capacity closer to the theoretical adsorption capacity of WK11 (~550 $g_{ethanolamine}/kg_{wK11}$) could be reached after the first adsorption stage. This value reduced and stabilized at an operating adsorption capacity of ~150 $g_{ethanolmine}/kg_{WK11}$ throughout the following five cycles. Throughout all cycles a high ethanolamine purity of >95 wt % was delivered. The ethanolamine collected in these high-purity fractions accounted for ~85 wt % of the adsorbed ethanolamine, thus demonstrating a high yield. The missing wt % of the ethanolamine was collected in the water fractions obtained during the water removal stage between the adsorption and desorption stages.

Example 2: Isolation of Ethanolamine Using a Non-Functionalized Adsorbent Diaion™HP2MGL (Comparative Example)

Figure 1B:
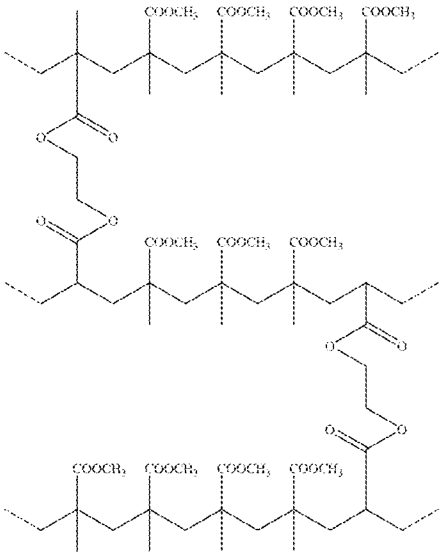

Diaion™ HP2MGL (HP2MGL) is a non-functionalized porous methacrylate-based adsorbent. Its matrix is almost identical to the one of WK11. Its chemical structure is shown in FIG. 1*b*. The carboxyl groups of WK11 are esterified in HP2MGL, and also different cross-linking agents are used: divinylbenzene for WK11 and ethylene glycol for HP2MGL.

The adsorption experiment performed with HP2MGL under the same conditions as in Example 1 revealed that ethanolamine could not be adsorbed in the absence of a carboxyl group. The feed and the eluents collected after they had left the column or were in the column when the feed stream stopped had identical concentrations of ethanolamine, so no adsorption took place. Table 2 compares the adsorption capacities (in $g_{ethanolamine}/kg_{WK11}$) of WK11 and HP2MGL for ethanolamine.

TABLE 2

| Adsorbent | Ethanolamine capacity [$g_{Ethanolamine}/kg_{Dry\ WK11}$] |
|---|---|
| Diaion ™ WK11 | 458 |
| Diaion ™ HP2MGL | 0* |

*Identical concentrations in feed and eluents.

HP2MGL is classified by the manufacturer as a strongly hydrophilic adsorbent, but ethanolamine was so much more hydrophilic that it preferred water to the adsorbent. This demonstrates the importance of the carboxyl groups at the adsorbent for isolation of amines by the present method of invention.

Example 3: Examination of Capacity Reduction

A sample of the adsorbent was collected after the third adsorption-desorption cycle for FT-IR analysis to determine the reason for the capacity loss after the first cycle. The collected sample was divided by two, one of which was washed with a 1 M HCl solution to chemically desorb the thermally non-desorbed ethanolamine. The sample was then rinsed with Milli-Q® water and acetone, and dried before the FT-IR analysis. A sample of the fresh adsorbent was also rinsed with Milli-Q® water and acetone, and dried for the FT-IR analysis to serve as reference. The infrared spectra were recorded with a Tensor II FT-IR spectrometer (Bruker, Ettlingen, Germany) equipped with a glow bar source and a DTGS detector. An attenuated total reflectance unit (ATR, Specac, Riverhouse, Kent, UK) was positioned in the optical path of the spectrometer. The ATR unit was equipped with a plane, horizontally oriented 1.4 mm×1.4 mm diamond. For the measurement of solids, the sample would be brought into intimate contact with the diamond surface by applying some additional pressure with a screw equipped with a sapphire tip. 80 scans were accumulated for both the sample spectrum and the background spectrum (empty diamond). The resulting absorbance infrared spectrum was calculated using these two measurements.

Figures 2A, 2B, 2C:
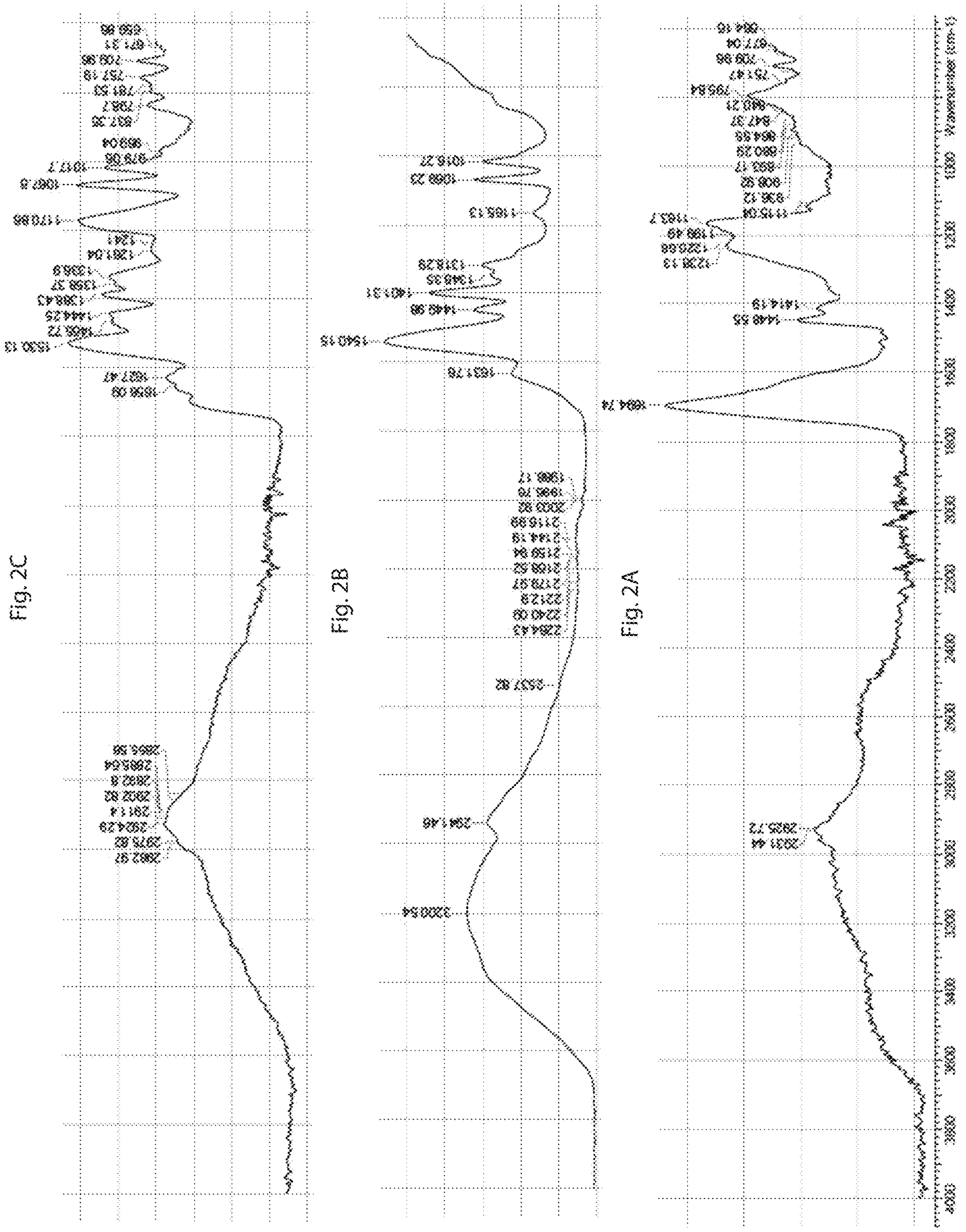

FIGS. 2A-C show the FT-IR spectra of the fresh adsorbent (FIG. 2A), the adsorbent after the three cycles (FIG. 2B), and the adsorbent after the three cycles washed with HCl, Milli-Q® water and acetone and dried (FIG. 2C). In the spectrum of the fresh adsorbent (FIG. 2A), predominantly, the C═O stretching band of the carboxyl group at 1695 $cm^{-1}$ can be observed. In the spectrum of the adsorbent after the third cycle (FIG. 2B), some prominent features of ethanolamine, especially the C—N (1069 $cm^{-1}$) and C—O (1016 $cm^{-1}$) stretching bands, can be observed. Furthermore, an $NH_2$ bending at 1540 $cm^{-1}$ is present. The C—H stretching vibrations of the $CH_2$ groups are also visible at 2941 $cm^{-1}$. The broad band with a maximum at 3200 $cm^{-1}$ can be assigned to O—H and N—H stretching vibrations. At 1631 $cm^{-1}$, a small band is visible, which is corresponding to a C═O stretching vibration of an amide. In the IR spectrum of the washed adsorbent after the third cycle (FIG. 2C), some signals at 1695 $cm^{-1}$ are visible, most likely due to minor residual amounts of non-desorbed ethanolamine. Furthermore, the amide band at 1627$cm^{-1}$ is still visible. This indicates that some ethanolamine is covalently attached to the adsorbent via an amide bond.

It can be concluded that both the non-desorbed ethanolamine and the amide formation have contributed to the adsorption capacity loss after the first cycle. It is assumed that the adsorbent particles neighbouring the jacket underwent permanent capacity loss due to the formation of amides. However, as a porous methacrylate-based matrix is a poor heat transfer medium, the same adsorbent particles neighbouring the jacket acted as a heat shield to protect the rest of the adsorbent bed from permanent capacity loss. An improved heat transfer is therefore needed to desorb the non-desorbed ethanolamine from the intact carboxyl ethanolamine complexes.

Such an analytical procedure using FT-IR is a simple technique to design and optimize the column for any amine of interest. The column diameter, the jacket temperature and the nitrogen temperature can be adjusted accordingly to optimize the heat transfer, thus maximize the amine desorption and minimize the amide formation.

The invention claimed is:

1. A method for the isolation of an amine from an aqueous solution thereof, the method comprising:
- contacting the aqueous solution of the amine with an adsorbent functionalized with carboxyl groups;
- removing water from the adsorbent; and
- thermally desorbing the amine;
- wherein the amine is an alkanol amine.

2. The method of claim 1, wherein the alkanol amine is ethanolamine.

3. The method of claim 2, for the isolation of ethanolamine, wherein the method comprises synthesising ethanolamine by fermenting a carbon source in the presence of an ethanolamine-producing microorganism to provide a fermentation composition comprising ethanolamine.

4. The method of claim 2, wherein a washing step is added after contacting the aqueous solution of the amine with the adsorbent functionalized with carboxyl groups.

5. The method of claim 2, wherein the adsorbent is thermally stable up to at least 150 °C.

6. The method of claim 2, wherein the adsorbent has a porous methacrylate matrix.

7. The method of claim 2, wherein the aqueous solution of the amine is a fermentation composition.

8. The method of claim 1, wherein a washing step is added after contacting the aqueous solution of the amine with the adsorbent functionalized with carboxyl groups.

9. The method of claim 1, wherein the adsorbent is thermally stable up to at least 150 °C.

10. The method of claim 1, wherein the adsorbent has a porous methacrylate matrix.

11. The method of claim 1, wherein the aqueous solution of the amine is a fermentation composition.

12. The method of claim 1, wherein the step of removing water comprises flushing out with a compressed nitrogen stream.

13. The method of claim 12, wherein the compressed nitrogen stream for removing water is heated up to at least 70 °C.

14. The method of claim 12, wherein for removing water a container comprising the adsorbent is heated up to at least 80 °C.

15. The method of claim 1, wherein a compressed nitrogen stream for thermally desorbing the amine is heated up to at least 100 °C.

16. The method of claim 1, wherein for thermally desorbing the amine a container comprising the adsorbent is heated up to at least 120 °C.

17. The method of claim 1, wherein the thermally desorbed amine is collected in a cooled condenser.

18. The method of claim 1, wherein the thermally desorbed amine has a purity equal to or greater than about 60%, or greater than about 70%, or greater than about 80%, or greater than about 90%, or greater than about 95%.

19. The method of claim 1, wherein the yield of thermally desorbed amine is equal to or greater than about 80%, equal to or greater than about 85%, or equal to or greater than about 90%.

20. A method for the isolation of an amine from an aqueous solution thereof, the method comprising:
- contacting the aqueous solution of the amine with an adsorbent functionalized with carboxyl groups;
- removing water from the adsorbent; and
- thermally desorbing the amine;
- wherein the aqueous solution of the amine is a fermentation composition.

* * * * *